(12) United States Patent
De Almeida et al.

(10) Patent No.: US 7,163,737 B2
(45) Date of Patent: *Jan. 16, 2007

(54) ABSORBENT COMPOSITION OF MATTER FOR ODORIFEROUSE SUBSTANCES AND RELEASER OF DIVERSE ACTIVE INGREDIENTS AND ARTICLES INCORPORATING SAME

(76) Inventors: Jose Represas De Almeida, Bosque de Duraznos #65-305, Col. Bosques de las Lomas (MX) DF 11700; Genaro Casas Jassan, Bosquee de Duraznos No. 65-305, Col. Bosques de las Loas (MX) CF 11700

( * ) Notice: Subject to any disclaimer, the term of this patent is extended or adjusted under 35 U.S.C. 154(b) by 120 days.

This patent is subject to a terminal disclaimer.

(21) Appl. No.: 10/642,920

(22) Filed: Aug. 18, 2003

(65) Prior Publication Data

US 2004/0078048 A1   Apr. 22, 2004

Related U.S. Application Data

(63) Continuation-in-part of application No. 09/856,196, filed as application No. PCT/MX00/00034 on Sep. 4, 2001, now Pat. No. 6,635,344.

(30) Foreign Application Priority Data

Sep. 17, 1999  (MX) ..................... 998523

(51) Int. Cl.
*B32B 5/16* (2006.01)
*A61F 13/53* (2006.01)

(52) U.S. Cl. .................. 428/323; 428/327; 604/367; 604/374

(58) Field of Classification Search ........ 428/326, 428/402, 323, 327; 119/171, 172; 241/24.1, 241/24.2; 502/404, 439; 604/358, 367, 604/374
See application file for complete search history.

(56) References Cited

U.S. PATENT DOCUMENTS

| | | | |
|---|---|---|---|
| 3,617,564 A | 11/1971 | Vander Hooven et al. | |
| 3,921,581 A | 11/1975 | Brewer | |
| 4,053,112 A | 10/1977 | Vander Hooven et al. | |
| 4,296,709 A | 10/1981 | Schulein, Jr. | |
| 4,519,340 A | 5/1985 | Dickey | |
| 5,062,954 A | 11/1991 | Leedy et al. | |
| 5,064,407 A | 11/1991 | Peiffer | |
| 5,152,251 A * | 10/1992 | Aukeman et al. | 119/171 |
| 5,160,629 A | 11/1992 | Brown | |
| 5,207,389 A * | 5/1993 | Hall et al. | 241/3 |
| 5,878,696 A | 3/1999 | Gerling et al. | |
| 5,891,937 A | 4/1999 | Berg et al. | |
| 6,053,125 A * | 4/2000 | Kory et al. | 119/171 |
| 6,635,344 B1 * | 10/2003 | de Almeida et al. | 428/326 |

FOREIGN PATENT DOCUMENTS

| | | |
|---|---|---|
| EP | 0470 596 | 2/1992 |
| ES | ES419 420 | 4/1976 |
| FR | 2598280 | 11/1987 |
| WO | WO-98 54956 | 12/1998 |

* cited by examiner

*Primary Examiner*—H. Thi Le
(74) *Attorney, Agent, or Firm*—Peter J. Rashid; Warn, Hoffmann, Miller & LaLone

(57) ABSTRACT

A new product is described characterized by its qualities to absorb undesirable scents present in the air, while serving at the same time as a carrier for aromas, fragrances, flavorings, repellents, attractants and other active ingredients. The active ingredients are gradually released by the carrier, which is compatible with the environment and current tendencies towards the use of organic and biodegradable products. The composition comprises a carrier and an active ingredient. The carrier is characterized as being particles obtained from the milling, separation, air wash and classification of the different fractions obtained from corncobs. An article of manufacture and a method of making the article containing the absorbent composition of matter is also disclosed.

17 Claims, No Drawings

ABSORBENT COMPOSITION OF MATTER FOR ODORIFEROUSE SUBSTANCES AND RELEASER OF DIVERSE ACTIVE INGREDIENTS AND ARTICLES INCORPORATING SAME

CROSS-NOTING TO RELATED APPLICATIONS

This application is a Continuation-In-Part application of Application Ser. No. 09/856,196, filed on Sep. 4, 2001 now U.S. Pat. No. 6,635,344, which claims the benefit of PCT Application No. PCT/MX00/00034, filed Sep. 13, 2000, which claims the benefit of Mexican Application No. 998523, filed Sep. 17, 1999, the entire contents of which are herein incorporated by reference.

BACKGROUND OF THE INVENTION

1. Field of the Invention

The present invention relates to odor absorbing and controlling compositions in powder form which are useful in articles such as sanitary napkins, pantiliners, catamenials, diapers, bandages, adult incontinence garments, and the like. The odor-controlling composition herein, as incorporated in the aforementioned articles, is designed to combat a broad spectrum of odoriferous materials, including sour, menses, feces and "ammonia" type, odors.

2. Description of the Related Art

The search by mankind for absorption of unpleasant aromas and scents in the air that we breathe is as old as civilization. The earliest documents come from the Egyptians that used substances like charcoal, to absorb from the air the scent of the cadavers in the mummification process.

Over the centuries these processes of purification for breathable air evolved in their technique, particularly at the beginning of the XX century due to the advent of toxic gases for military purposes. This evolution consisting in the filtration of breathable air has progressed to satisfy military and industrial necessities. Quick advances in the state of the art were made during the second half of the XX century, to improve the quality of the air in closed spaces, due to the contaminants in the air, generated by industry, transportation and in general by modern human activities. These filtration and purification systems in general are expensive and active in nature, requiring energy to circulate the air for its filtration.

On the other hand, the evolution of passive systems has been slow and not as effective as that of the active systems. Passive systems do not require energy to absorb scents; fans or forced air through filters are not necessary to absorb gases or undesirable substances in the air. Passive systems are characterized to be substances or products that exposed to the environment, absorb, adsorb (accumulation on the surface) or react chemically to eliminate undesirable scents, gases or particles from the air.

The necessity to counteract or to eliminate, effectively and economically, the undesirable odors in the air has increased along with population growth, especially in urban concentrations since this is where the largest amount of pollutants and substances that bother human smell are generated. Examples of patents addressing this problem, are U.S. Pat. Nos. 5,944,704; 5,932,495; 5,932,147; 5,891,508; 5,861,147; 5,856,248; 5,807,364; 5,782,409; 5,733,272; 5,714,137 and the 5,593,670.

Examples common to the necessity of counteracting these polluting agents that cause bad odors are: the elimination of the aroma of tobacco smoke and its smell that impregnates closed spaces, such as houses, offices and automobiles. The malodor of garbage in kitchens, houses and buildings. The necessity to absorb or to neutralize scents during storage of foods, ranging from domestic to commercial and industrial refrigerators. The previous examples are just a small sample of the dynamic and ever more complex universe of human beings and pets, cohabiting and using progressively more consumer goods in continuously reducing spaces.

In the combat of malodor scents, the most common and oldest is the one characterized by the use of substances that contain perfumes to mask scents. The masking of scents is the concealment of one smell by another, usually a malodor. However, the preferences for different aromas vary according to the individual and require relatively large amounts of perfume to counteract smelly malodor aromas.

Other forms of controlling malodor are, for example, the use of chemical substances. These processes are known in the state of the art as degradation by oxidation, where oxidizing agents such as: Chlorine bleach, Sodium hypochlorite, Chlorine Dioxide, and Potassium Permanganate are used. Other forms use degradation processes for reduction of malodor, these use active ingredients such as, Sodium Bisulfate to reduce malodor. These substances can be dangerous and aggressive for humans if used in direct form or exposed to the environment, they may also be harmful if in direct contact to cloths and many different surface materials.

Another method for the control of malodor is the use of active ingredients designed to react with smelly or malodor substances, by using specific chemical groups. Examples of these substances are the biguanid polymers that are mingled with organic compounds that contain atoms N and/or S, as well as the esters of fatty alcohol's of Methyl Metacrylic that react with thiols, ammines and aldehydes. Their benefits are limited since they only react with certain very specific types of malodor.

Other types of well-known compounds are deodorants, in the state of the art these are antibacterial and fungicidal which destroy microorganisms that produce malodor. These compounds, typical in formulations of products for personal hygiene, are not effective in combating smelly substances that have already been generated and that do not come from sources like tobacco smoke or food.

Other forms of eliminating undesirable aromas from the air, are achieved, using absorbent substances or products. Malodor particles or compounds stick to their molecular structure; these chemical compositions are the cause of malodor. Other absorbent agents are characterized by admitting and retaining the malodor molecule inside their molecular structure. Among the more common absorbent agents are charcoal, alkaline compounds such as sodium bicarbonate, aluminum silicates and Zeolite. Some chemical substances are also absorbents, such as: Ciclodextrine whose intermolecular cavities admit small molecules of malodor. However, Ciclodextrin, especially when formulated in a watery solution, is considered fertile ground for microorganisms, given their important glucose content.

Finally it is necessary to consider that conceptually there are two forms of achieving reduction or elimination of malodor. The first is called a passive system, meaning that upon exposure to the environment, the active ingredient or the absorbent agent eliminates malodor scents from the surrounding air by contact. The second is an active system that achieves effectiveness by utilizing a mechanical devise. Most common are forced air systems that circulate air that in combination with absorbent or active ingredients, filter, absorb, perfume, or react chemically with malodor substances.

A variety of absorbent structures designed to be efficient for the absorption of body fluids such as blood, urine, menses, and the like, while also being sanitary and comfortable in-use are known in the art. Products of this type are generally disposable and comprise a top sheet material, an absorbent core, and a back sheet. Over the years different forms, sizes and thickness of such articles have been tried in an attempt to make the use of these articles more convenient and comfortable. Retention of liquids and or body fluids with such constructions can be quite good, while their odor absorption capacity can be lacking, creating a possible social embarrassment.

One aspect of sanitary products which has been researched for many years is that of odor control. Many body fluids have an unpleasant malodor, or develop such odors when in contact with air and/or bacteria for prolonged periods. Microbial action on proteins has been recognized as a source of malodor. Urine for example is a fluid that causes malodor due to microbial activity that can form ammonia from urea in excreted urine. The literature is replete with references relating to odor control in products such as diapers and catamenials. Thus far, malodor control has used technologies that inhibit microbial activity, or suppress malodors by masking them.

A considerable number of references relating to odor control substances or compositions in sanitary products. The following are illustrative examples:

U.S. Pat. No. 3,939,838 relates to active carbon, active silica, active alumina, ion exchange resin and chlorophyll.

EPO 348978 discloses an absorbent article comprising an odor control system wherein the neutral odor control particles are selected from carbon, clays, silica, zeolites and molecular sieves.

WO 91/12029 discloses the combination of zeolites and absorbent gelling materials to provide improvement in the control of ammonia odors.

EP-A-0509409 discloses an odor control mixture which includes at least basic and pH neutral odor absorbing particles, and optionally acidic odor absorbing particles.

U.S. Pat. No. 3,995,636 relates to a rapidly re-expandable hydrophilic polymeric.

U.S. Pat. No. 5,122,407 discloses an odor absorbing reagents are activated carbon, ABSCENTS (ABSCENTS is a registered Trade Mark) (synthetic zeolite), sodium bicarbonate and carbonates, bicarbonates, phosphates, biphosphates, sulfates and bisulphates of alkali and alkaline earth metals; ascorbic acid, boric acid, citric acid and maleic acid.

U.S. Pat. No. 5,797,891 relates to a saponin for use in the reduction and/or elimination of undesirable odors.

Most previously disclosed absorbents are not efficient in controlling body fluid malodor and repeat in different form the same ingredients. Active charcoal additionally has disadvantages of its use in sanitary products relate to its color and appearance.

Therefore, there is a need in art for a safe, cost effective and highly efficient method of body fluid malodor absorption that is easily incorporated into an article of manufacture, such as a sanitary product that contains an absorbent composition of matter for odoriferouse substances.

SUMMARY OF THE INVENTION

The functional objective of this invention, is that this composition of matter gathers three simultaneous qualities: 1) absorbs undesirable scents from the air, 2) simultaneously releases into the air different types of active ingredients, usually but not limited to pleasant aromas, 3) Operates efficiently and economically by being a passive agent that does not require use of energy and it's associated operating cost.

Additionally it is necessary to contemplate other factors that are concurrent in the present invention and that are part of the new product, object of this invention in it's functional aspects:

First; Current tendencies prefer the use of organic and biodegradable materials, such is the case of this absorbent carrier that while absorbing malodors and releasing active ingredients into it's surrounding, is compatible with the environment and easily disposable and recyclable in nature.

Second; Covered under the concept of aromas we find pleasant smelling substances perceivable to the human sense of smell, as well as other substances that without being significantly disagreeable to humans may be used as repellents or attractants for other species. The composition of matter object of this invention can also be used as a carrier for repellents or attractants to species like insects, microorganisms, reptiles, mammals, etc.

The concept of the new product derived from the present invention, is enlarged in its range of applications. For example, uses in agriculture, home and industry are possible by combining its qualities to absorb malodor and gradually release an aromatic substance to repel plagues of insects like cockroaches in kitchens or mosquitoes as well as other agricultural crop damaging insects. Good results are obtained by combining a substance like Nepetalactone, known for its qualities as a repellent of cockroaches or garlic known for its qualities as a repellent for garden or agriculture damaging insects, with this absorbent carrier. Additionally the absorbent carrier has the capacity to gradually release these forms of repellent aromas providing for a long lasting product; malodor, if present is also absorbed. Inversely, attractant substances can be used, being of particularly useful application for household pets, for example, the use of an attractant aroma or fragrance in the production of cat litter.

Third; the absorbent agent can be combined with other chemical substances whose properties allow them to react chemically with aromas present in the air. This includes the use of substances not perceived by human smell. Such as oxidizing agents or reducers that can help neutralize the concurrence of diverse aromas, like those present in a refrigerator. Simultaneously, the aroma absorption capacity of the carrier comes into effect resulting in a refrigerator that doesn't smell.

Another example for the use of the composition of matter subject of this invention, is its use for medicinal and therapeutic use. As is the case of aromatherapy, where the carrier releases into the air of a room, automobile, or office, aromas of medicinal type in accordance to the results a user is trying to achieve, for example: Aroma of thyme, eucalyptus or other to alleviate breathing congestion.

Fourth; The product object of the present invention fulfills the qualities of absorption of malodor and/or the release of aromas or fragrances in a passive way, when being exposed to the environment in any container that allows its contact with the air around it. The new product can also be used as a substantial component in active systems, since it can be adapted to all type of air conditioning, heating, air filtration, air care, industrial or commercial spaces as well as transportation vehicles. Functionality is mostly dependent on the use of an appropriate container that adapts to the required air intake of the system in question.

The qualities of the new product are more obvious and more effective in active systems of air filtration and conditioning, characterized by recycling air in relatively reduced spaces, such as automobiles, airplanes and public transportation vehicles. The intensity and duration of the aroma or fragrance released in the air through active systems, can be controlled by the concentration of aromas, fragrances or active substances to be used as well as it's adequate formulation, according to the knowledge available for the state of the art.

The present invention relates to a novel method for decreasing odors emanating from sanitary articles that control body fluids such as menses, vaginal discharges, urine, and the like, with an odor absorbing composition of matter comprising the woody ring and chaff portions of the corn cob. The composition can be used alone or in combination with active ingredients such as polymers, fragrances, perfumes, flavors, reducers, neutralizers and anti bacterial, in either a liquid or a solid state.

The invention thus provides an innovative method of controlling malodor in articles, such as sanitary napkins, pantiliners, cateamenials, diapers, adult incontinence garments, underarm shields, toilet tissues, and the like, wherein the odor absorbing composition of matter is dispersed, mixed or applied to the construction of these articles. The resulting odor absorbing products are excellent in terms of malodor absorbency and reduction compared to conventional products most commonly composed of cellulose with or without additives such as super absorbent polymers (SAP) and fragrances.

Additionally, the composition of matter in the present invention provides for a controlled time release of the different active ingredients applied to the preferred embodiment (corn cob particles), thereby making the use of these sanitary products more comfortable to users over a prolonged period of time.

DESCRIPTION OF THE PREFERRED EMBODIMENT

The preferred embodiment of the product object of the present invention consists of two basic elements: first, a carrier characterized by its great capacity for odor and malodor absorption, and gradual release of other active substances toward the air or surrounding atmosphere. Second, one or more chemical, natural or synthetic elements that added to the carrier complete diverse functions, according to the desired results (perfume surrounding air, react with undesirable substances present in the air, liberate therapeutic, repellent or attractant chemical agents).

The carrier which is the preferred embodiment of the product in the present invention is a material obtained from the threshed ear of corn (Zea Maiz) whose special physical and chemical qualities allow the previously described functions, of absorption and gradual release. To obtain the different components that comprise the threshed ear of corn, an industrial process, well known in the state of the art is required, which consists of separation, classification and sizing of each one of the components that constitute corncobs.

The threshed ear of the corn, also known as "olote" in Mexico, "spiga de maiz" in Castilian, corncob in English, "sabugo" in Portuguese and "balle de maïs" in French, if cut transversely is constituted by three concentric ring. Starting with the inner ring, they are known in English as pith, woody ring and chaff. The material of the present invention uses the woody ring and chaff portions.

The woody ring, as well as the chaff portion, has similar characteristics, both can be used as carriers for active ingredients as described in the body of the present invention. The main differences reside in the difference of absorption capacity and in the particle hardness. Other differences exist and are described below.

In order for the woody ring to comply with the requirements of the present invention it must have the following characteristics: woody ring should be 99% free of other cob particles, it should have no more than 1% dust or fines (the product should be air washed). It must be subjected to heat treatment that guarantees microbiology content and moisture levels under 10%. For correct functionality, the particle size should be uniform in size and ranges should not exceed a maximum of 2380 microns and a minimum of 250 microns.

The woody ring of corncobs is characterized by the following: a hardness of 4.5 on the Mohs scale, a fast absorbency of oil (for example soybean oil) of 1 to 1 on weight basis and the typical molecular structure of a natural fiber. Ideally particle sizing for the present invention should be between the following ranges: 1) retained or larger than a mesh of 2380 microns, 2) particles between 2380 and 1191 microns, 3) particles between 1191 and 841 microns, 4) particles between 841 and 420 microns.

The main characteristic of the particle size is the surface area that each one represents; for example, particles between 1410 and 841 microns have an average surface area of 5.88 square meters per gram. Particles between 841 and 420 microns have an average surface area of 7.20 square meters per gram. This characteristic is decisive in the qualities of absorption of different substances on the part of the carrier that embodies the product object of the present invention.

It is necessary to highlight that woody ring particles are characterized by having a structure that seen on an electron microscope resembles that of a sea sponge. One can infer that this type structure has capacity to admit and retain substances of small and large molecular size. This allows superior qualities of absorption in comparison to other products such as Cyclodextrin that as is known in the state of the art, only admits malodor molecules of small size.

The separate and classified sizes of woody ring have unique qualities for the absorption of scents from the air in contact with them. To illustrate this, diverse laboratory tests were made with surprising results as follows:

EXAMPLE #1

A 100 gram portion of mature Camembert cheese, a 20 gram portion of bacon and a 10 cm dish containing 25 grams of woody ring particles sized between 1410 and 841 microns where all placed in a sealed glass container. Another glass container with the same components except for the woody ring particles was also prepared as a control sample. Both glass containers were inspected at intervals of 24 hs, 3 days, 5 days and 8 days; the container with the absorbent material practically didn't manifest the characteristic scent of the decomposition of products contained, while the control glass container presented potent and unpleasant scents.

EXAMPLE #2

10 grams of tobacco where incinerated in two sealed glass containers. One of the containers had a 10 cm diameter dish containing 10 grams of woody ring, sized between 1410 and 841 microns. The other container remained as a control sample. After 24 hours both containers where opened. The container with the absorbent woody ring particles did not present the characteristic scent of tobacco, while the control sample presented potent scents characteristic of tobacco smoke.

In both tests the evaluation of the scents or aromas were carried out by the authors of the present invention, as well as by a professional perfumist whose educated sense of the smell surrendered an objective opinion of these tests.

The characteristics of the Chaff portion of the corncob are similar to the woody ring portion in its ability to function as a carrier for fragrances and other active ingredients. The most distinguishing differences are: 1) more absorption; between 1.5 and 3 times it's weight in oil, 2) Particles size between 841 and 73 microns and 3) less particle flowability. Woody ring particles are rounder in shape than chaff and therefore flow better.

This physical difference between woody ring particles and chaff particles is translated into functional differences in the ability to absorb undesirable scents from the air. Additionally the granular form of the woody ring allows for more interparticle space for air-flow. While the smaller closer chaff particles allow less airflow.

Both woody ring and chaff are characterized by having an almost neutral pH, in the order of 6. This quality makes it an ideal inert carrier with all type of substances, since it does not react with active ingredients. Some other types of carriers have to be disactivated first to neutralize their pH content.

The physical and chemical characteristics of corncobs are not favorable for the development of microorganisms, therefore not providing fertile ground for bacteria or fungi that in turn cause malodor or disagreeable scents. It is known in the state of the art that a whole corncob can be stored without cover for periods of one year.

The functional differences of the woody ring portion (flowability and larger interparticle space) and that of the chaff (more absorption) allow for a great diversity of applications and use. These corncob fractions can be used combined or separately, for different applications, that are described for the absorbent carrier that integrates the product object of the present invention.

For example, if the functional objective, is the absorption of an active substance to be slowly released in the air and at the same time allowing the flow of malodor air to be absorbed, the suitable product is the one obtained from the woody ring. If on the contrary the functional object is to achieve absorption of an active substance to be slowly released in the air and the absorption of malodors or scents is not important, the elected product would be the chaff portion.

Other approaches to select the corncob fraction can be: the convenience of not having powders or fines. An example of such an application is the integration of the absorbent agent to active filtration systems where the use of the product from the woody ring is most suitable. If the active ingredient required is thick in nature or if product were required to be molded in a three-dimensional object (including the making of pellets), one would be inclined to select the chaff portion.

On the other hand, and a substantial element of the composition of matter, object of the present invention, are the active substances or ingredients to be used. These can be aromas, perfumes, flavors or other natural or chemical agents that are integrated to the product derived from the composition of matter object of the present invention. In general these substances are available in a liquid, powder or granular state and depending on the active agents chemical constitution, soluble in oil or water.

Under these conditions the absorbent carrier, depending on the type of active ingredients used, can absorb a larger or smaller quantity of said agent. This depends primarily on the size of the active ingredient molecule size, the absorbent carriers gradual release will also depend on this molecular size. The absorption of malodor or scents is simultaneously achieved. The intensity, duration and brightness of the aroma, with fragrances, will depend on factors of the active ingredient or agent's composition. For example, larger molecular size is equal to longer duration, while the presence of smaller molecular sizes such as those in an ester evaporate quickly.

Some examples for the formulation of the absorbent carrier with active substances in a liquid state are:

EXAMPLE #1 for fragrances, perfumes and therapeutic aromas, generally using a base of polyvinyl glycol, light mineral oil or microencapsulated powder or granular base, the concentration on a weight basis of the woody ring to active ingredient, is from 0.01% to 18%. A larger amount saturates the absorbent carrier and product flowability is greatly reduced. The concentration on a weight basis of the chaff portion to active ingredient is from 0.01% to 36%.

EXAMPLE #2 for repellents and attractants, generally in oleaginous or microencapsulated powder or granular bases such as Givaudans Flavor Burst™ products, the recommended concentration ranges, for the woody ring as well as the chaff portion, are similar to the previous example. Concentrations depend on the active ingredient or agent used and the functionality desired in the end product.

EXAMPLE #3 for oxidizers and chemical reducers or neutralizers, generally in a liquid or solid microencapsulated powder or granular base, the concentration ranges on a per weight basis, both for woody ring and chaff are from 0.05% to 5% of active ingredient or substance. Being that the determinant factor is not the capacity of carrier absorption, but rather the capacity to stay stable and not be affected by the active substance.

EXAMPLE #4 for antibacterial and fungicidal use, when these are in a water, oleaginous or microencapsulated powder or granular base, the proportion of active ingredient or agent on a per weight basis to absorbent carrier is the same as that of example #1. When the active ingredient uses a water base, the concentrations on a per weight basis can range from 0.01% to 25% with the woody ring fraction and 0.01% to 50% with chaff. The concentration to choose will be determined by the experience of whom ever prepares formulations according to the known state of the art.

Additionally as mentioned in previous examples, the formulation of the composition of matter or product object of the invention, can be made using liquid based active ingredients added to the absorbent carrier. The possibility also exists for the use of solid materials as active ingredients, usually in the form of pure or microencapsulated products. This variation allows more flexibility in the absorbent carriers applications. It can also take advantage of factors like stronger concentrations of active ingredients. Many pure substances come in solid form; the use of a liquid as diluent or dispersant of the pure substance implies a reduction in its concentration or strength. For example table salt NaCl is more intense to the palate than its version diluted in water, commonly called brine.

On the other hand the use of active ingredients in solid state can adhere and/or adsorb to the surface of the absorbent corn cob carrier, allowing it to use a larger proportion of it's inner absorbent capacity for malodor or other applications. The opposite occurs when using active ingredients in a liquid state, since these occupy more of the corncob carriers odor absorbent capacity thus partially reducing it's ability to absorb undesirable malodor.

The option of using active ingredients in solid state instead of liquid, is possible with the concurrence of 4 basic elements: an absorbent carrier, constituted by a fraction derived from corncobs, an active ingredient or agent that is in liquid or solid state; a combination resulting from the mix of a mineral or organic carrier with a liquid base active ingredient and finally, a substance that assures that, the active ingredients absorb or adsorb to the corncob carrier (avoiding the separation among carriers or agents and assuring correct homogeneity, functionality and dispersion).

To exemplify the above-mentioned we describe two practical examples. The results obtained, using two types of active ingredients one in liquid form and the other solid, both dispersed in the corncob carrier; woody ring sized between 1410 and 841 microns was used. The liquid active ingredient is a concentrated floral fragrance perfume using polyvinyl glycol as a carrier.

EXAMPLE #5

Corncob carrier mixed with an active ingredient in a liquid base. The density of the active ingredient determined a saturation point of 18% on a per weight basis to the corncob granules. 180 grams of active ingredient where mixed with a kilogram of corncob carrier. This proportion maintains carrier flowability, absorption of odors and slow release of active ingredient (fragrance).

Results: the perfuming active ingredient, was released gradually and perceived smell lasted 30 days. The corncob carrier continued absorbing scents in the air after 30 days.

EXAMPLE #6 two active ingredients; one utilizing an encapsulated active ingredient, commercially available, like Givaudan fragrance or flavor, in powder form and the other, using a laboratory sample, made by mixing Silicon Dioxide (SiO2), in proportion of 1 to 4 on the base of liquid active ingredient to Silicon Dioxide weight. The absorbent corncob carrier was impregnated with an adherent coating, in this case consisting of a 0.5% per weight basis, foamed solution of anionic surfactant with water. Once the corncob carrier was mixed with the foam, an adherent coating of foam formed on the corncob granules. Immediately after which the active ingredients in solid form where added. The active ingredient particles adhered to the coating and allowed for a homogeneous mixture without separation.

Results: In both cases the adhesion of solid particles to the corncob granules allowed a more intense and prolonged duration of the perfuming scent, which was slowly released over a 60 day period, in comparison to the 30 days obtained in example #5 with a liquid active ingredient perfume mixed directly with corncob granules. In both cases the corncob absorbed odors in the air even after 60 days.

Both examples, one with liquid and the other with solid active ingredients were performed at the same time. The new product was exposed to the air by placing it in a 40 cm×5 cm dish. The product was placed in two separate rooms measuring 3×4×2.4 mts.

The adherents used to form a coating on corncob particles are within the following ranges:

EXAMPLE #7

Using surfactants as adherent coating: anionic, cationic and amphoteric can be used. The formulation is: foam obtained from adding water to 0.02% to 5% of surfactant by weight. The quantity of foam on a per weight basis to corncob woody ring fraction (carrier) is between 0.5% and 3.5%. Larger proportions do not allow for an appropriate mixture when adding active ingredients in solid form.

EXAMPLE #8

Using mineral oils as an adherent coating; they should be highly refined preferably odor and colorless; viscosity on the Saybolt scale (SUS/210 F) should be between 40 and 300. The concentration of mineral oil by weight to woody ring is between 0.5% and 18%.

Finally active ingredients can be polymers, perfumes, oxidizers, attractants, repellents, reducers, antibacterials, etc, in solid form. These ingredients are mixed and dispersed with the granular corncob carrier sized between 37 and 250 microns. The quantity of solid active ingredient dispersed should be between 1% and 40% per weight basis.

In conclusion, the incorporation of corncob fractions mentioned with active ingredients whether chemically synthesized or natural, improves the qualities and functionality that both elements have for themselves separately. However, the use of corncob fractions as absorbent of odoriferous substances from the environment is also a novel concept. The forms of carrying out the mixture or integration of these elements can vary according to the circumstance. The types of active ingredients that will be used depend on the functional objective that is pursued, equipment available and the experience of those skilled in the art.

The use of corncob fractions as absorbent of odoriferous substances can be used a variety of articles of manufacture for controlling malodor, such as sanitary napkins, pantiliners, cateamenials, diapers, adult incontinence garments, underarm shields, toilet tissues, and the like, wherein the odor absorbing composition of matter is dispersed, mixed or applied to the construction of these articles. For example, the corncob fractions in the form of powder are dispersed in the fluff cellulose within the sanitary articles. The powder is dispersed into the fluff cellulose by conventional means, such as an augur or the like. Virtually all manufacturing plants that manufacture sanitary articles have augers mounted on the production line because the manufacturing plant commonly disperses a super absorbent polymer (SAP) which is a powder that gels with a liquid, such as urine or the like.

The following experiments in controlling malodor were conducted in different sanitary articles of common use; a women's sanitary napkin and an adult diaper, both having incorporated the odor controlling composition of matter of the present invention.

Experiment #1 Feminine malodor reduction; trials using pairs of same brand feminine sanitary napkins, sample A incorporating the odor controlling composition versus B not incorporating odor controlling composition. 15 ml. of feminine menses which is a larger than the average 7.5 ml. discharge was applied to each. Samples where placed in separate closed receptacles for 15 minutes to stabilize before measurement of malodor. Four repetitions of each sample where tested. Measurement procedure consisting of GC/Mass Spectrometry having previously identified the malodor causing compounds, with the following results:

On average after 15 minutes: Sample A incorporating the odor controlling composition showed a 95% reduction of malodor, as compared to the B control sample not incorporating the odor controlling composition that showed only a 25% reduction of malodor.

The amount of malodor reduction was further confirmed by professional perfumist who confirmed highly reduced almost unnoticeable sensory perception of the malodor present in sample A with applied odor absorbent when compared to the B control sample.

Experiment #2 Humane urine trials where performed using two same brand adult diapers. Urine was applied to both in the amount of 500 ml which is a larger amount than the average human discharge. Samples where placed in separate closed receptacles for 15 minutes to stabilize before measurement of malodor. Four repetitions of each sample where tested. Measurement procedure consisting of GC/Mass Spectrometry having previously identified the malodor causing compounds, with the following results:

On average after 15 minutes: Sample A incorporating the odor controlling composition showed a 80% reduction of malodor, as compared to the B control sample not incorporating the odor controlling composition that showed only a 21% reduction of malodor.

The amount of malodor reduction was further confirmed by professional perfumist who confirmed highly reduced almost unnoticeable sensory perception of the malodor present in sample A with applied odor absorbent when compared to the B control sample.

In conclusion, incorporating the odor absorbing composition matter of this invention significantly reduces the most common malodors emanating from human body fluids, and is therefore a novel and desirable addition to sanitary products that will allow for more comfortable usage by consumers while being cost effective.

While the invention has been specifically described in connection with certain specific embodiments thereof, it is to be understood that this is by way of illustration and not of limitation, and the scope of the appended claims should be construed as broadly as the prior art will permit.

What is claimed is:

1. An article of manufacture containing an absorbent material of odoriferous substances, said absorbent material comprising a carrier consisting essentially of particles obtained from a woody ring and a chaff ring of a corncob having a moisture content below 10%.

2. The article of claim 1, wherein said article comprises one of a sanitary napkin, a pantiliner, a cateamenial, a diaper, an adult incontinence garment, an underarm shield and a toilet tissue.

3. The article of claim 1, wherein the particles of the carrier have a size ranging between 73 and 841 microns.

4. The article of claim 1, further comprising an active ingredient mixed with said carrier.

5. The article of claim 4, wherein a concentration of said active ingredient ranges between 0.01% to 50% by weight of the chaff and woody ring of the corncob.

6. The article of claim 4, wherein a concentration of said active ingredient ranges between 0.01% to 50% by weight of the chaff ring of the corncob.

7. The article of claim 4, wherein the active ingredient is selected from a group consisting essentially of polymers, fragrances, perfumes, flavors, reducers, neutralizers and anti bacterial, in either a liquid or a solid state.

8. The article of claim 1, wherein said carrier is impregnated with an adherent substance.

9. A method of manufacturing an article containing an absorbent material of odoriferous substances, said absorbent material comprising a carrier consisting essentially of particles obtained from a woody ring and a chaff ring of a corncob, having a moisture content below 10%, said method comprising the step of dispersing said absorbent material within a fluff cellulose of said article.

10. The method of claim 9, wherein said article comprises one of a sanitary napkin, a pantiliner, a cateamenial, a diaper, an adult incontinence garment, an underarm shield and a toilet tissue.

11. The method of claim 9, wherein said carrier has a content of less than 1% of fines by weight and a moisture content below 10%.

12. The method of claim 9, wherein the particles of the carrier have a size ranging between 73 and 841 microns.

13. The method of claim 9, further comprising an active ingredient mixed with said carrier.

14. The method of claim 13, wherein a concentration of said active ingredient ranges between 0.01% to 50% by weight of the chaff and woody ring of the corncob.

15. The method of claim 13, wherein a concentration of said active ingredient ranges between 0.01% to 50% by weight of the chaff ring of the corncob.

16. The method of claim 13, wherein the active ingredient is selected from a group consisting essentially of polymers, fragrances, perfumes, flavors, reducers, neutralizers and anti bacterial, in either a liquid or a solid state.

17. The method of claim 9, wherein said carrier is impregnated with an adherent substance.

* * * * *